(12) United States Patent
Eklund et al.

(10) Patent No.: US 6,800,061 B1
(45) Date of Patent: Oct. 5, 2004

(54) METHOD AND DEVICE FOR DETERMINING THE INTRAOCULAR PRESSURE, BY MEASURING THE CHANGING OF THE FREQUENCY CHARACTERISTICS

(75) Inventors: Anders Eklund, Umea (SE); Olof Lindahl, Umea (SE)

(73) Assignee: Bioresonator AB, Umea (SE)

( * ) Notice: Subject to any disclaimer, the term of this patent is extended or adjusted under 35 U.S.C. 154(b) by 135 days.

(21) Appl. No.: 10/069,115

(22) PCT Filed: Aug. 24, 2000

(86) PCT No.: PCT/SE00/01628

§ 371 (c)(1),
(2), (4) Date: Jun. 10, 2002

(87) PCT Pub. No.: WO01/15594

PCT Pub. Date: Mar. 8, 2001

(30) Foreign Application Priority Data

Aug. 31, 1999 (SE) .............................................. 9903099

(51) Int. Cl.[7] .................................................. A61B 3/16
(52) U.S. Cl. ........................................................ 600/402
(58) Field of Search ................................ 600/398, 399, 600/402

(56) References Cited

U.S. PATENT DOCUMENTS

| | | | | |
|---|---|---|---|---|
| 3,070,087 A | * | 12/1962 | Sittel | .......................... 600/402 |
| 3,192,765 A | * | 7/1965 | Keiper | ........................ 600/398 |
| 3,308,653 A | * | 3/1967 | Roth | ........................... 600/402 |
| 4,759,370 A | * | 7/1988 | Kozin et al. | ................. 600/398 |
| 4,930,507 A | | 6/1990 | Krasnicki et al. | |
| 5,375,595 A | | 12/1994 | Sinha et al. | |
| 5,766,137 A | * | 6/1998 | Omata | ......................... 600/587 |

OTHER PUBLICATIONS

"Intra-ocular pressure measurement device", Document SU982649, Ryazan Wireless Eng. Inst. Dec. 28, 1982 (Abstract), World Patents Index, London, U.K., Derwent Publications, Ltd.

* cited by examiner

*Primary Examiner*—Eric F. Winakur
(74) *Attorney, Agent, or Firm*—Bacon & Thomas, PLLC

(57) ABSTRACT

The present invention relates to a method and a device for measuring the pressure p in an eye, the so-called intraocular pressure. The method includes a contact body with a known geometry being pressed against the eye with a gradually increasing contact force F and that when the area of deformation of the eye A can be determined, the pressure can be obtained from the relation P=F/A, whereby the frequency characteristic of a contact body associated with a sensor system oscillating in resonance is read, the contact body is pressed against the eye to form a new system oscillating in resonance, the contact force and frequency characteristic for the new system is read, and the change in frequency characteristic is calculated. In this way, the pressure of the eye can be determined since the sought deformation area A is a function of the change $A(f_r ch\ ar!)$. The device has a contact body (4) for pressing against the eye (1) and a means (3) of determining the force with which the contact body is pressed against the eye, whereby the contact body (4) is part of a system oscillating in resonance, and the resonance system is connected to a means (9) for reading the frequency characteristic of the system.

8 Claims, 1 Drawing Sheet

Figure 1:
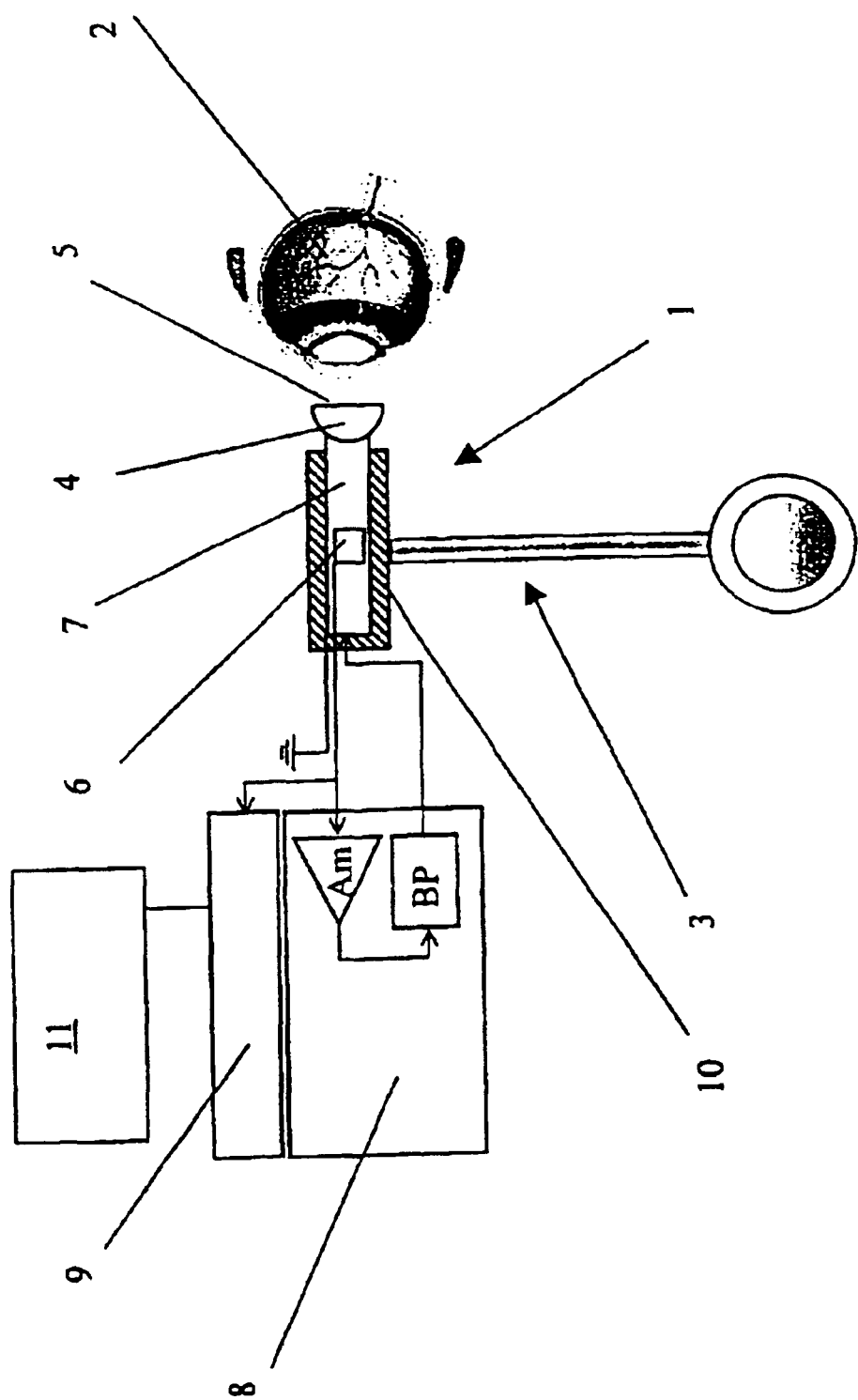

METHOD AND DEVICE FOR DETERMINING THE INTRAOCULAR PRESSURE, BY MEASURING THE CHANGING OF THE FREQUENCY CHARACTERISTICS

The present invention relates to a method and device for determining the internal pressure in an eye, the so-called intraocular pressure (IOP).

As long-term increased pressure in the human eye can lead to blindness, the pressure is routinely measured at all eye clinics. An applanation method is normally used at the clinic, e.g. the so-called Goldman applanation tonometer, which means that a probe is brought to press against the eye until a predetermined deformation is reached and the force required is read.

The basis of the pressure determination is then the known relation between pressure, force and area:

P=F/A where P=pressure, F=force and A=area

The internal pressure of the eye can thus be calculated from the contact force against the eye and the area of deformation of the eye.

To establish that a specified deformation (area) has been reached, a fluorescent chemical is introduced to the eye and the eye is illuminated so that changes in light reflection at deformation can be read.

Another method is used when the demand on accuracy is not so high. It is a method where a jet of pressurised air is used to deform the eye with a specified force, whereby the deformation is read by detecting light reflections. This method has no physical contact between a fixed object and the eye.

Both methods are based on a force deforming the eye, which the patient can experience as being uncomfortable or painful, even though local anaesthetic is used with, for example, the Goldman method.

In addition, the former method has shown to be sensitive to astigmatism, as light refraction is always employed during measurement of the deformation of the eye. The latter method has documented shortcomings in precision and is thus not used when the nominal pressure is to be determined, but is often used instead by opticians, etc., for an initial measurement of the magnitude of the pressure.

There is always a risk of damaging the eye, especially the cornea, when the eye is pressed. This is one reason why it is desirable to minimise the contact force against the eye. The lowest force possible is determined according to the equation above by the area or deformation that is needed for this area to be correctly detected. The light reflection method that is used to detect or read the area of deformation requires a relatively large area for a correct reading and thus an equivalent relatively large force.

It is the aim of the present invention to alleviate or overcome the disadvantages stated above for known methods and devices for measuring the internal pressure in an eye.

This aim is achieved with a method and device that is first mentioned above and that has the characteristics that are defined in the following independent claims.

These and further characteristics and advantages of the invention will become evident from the following detailed description of preferred embodiments of the invention, which constitute an example and as such are not limiting for the scope of protection of the invention. To simplify understanding, the text includes references to an enclosed drawing.

FIG. 1 shows schematically parts in a device according to one embodiment of the invention.

According to the present invention, a vibrating or oscillating contact body is pressed against the eye to determine the deformation of the eye.

We have found that changes in the frequency characteristic, between on the one hand a system oscillating in resonance and on the other hand the system partly brought into contact with an eye to form a new system oscillating in resonance, are dependent on the surface area of the contact.

One method for determining the pressure p in an eye, the so-called intraocular pressure, includes a contact body with known geometry being pressed against the eye with a progressively increasing force F and that when the deformation area A of the eye has been determined, the pressure is obtained from the relation P=F/A. New for the invention is to read the frequency characteristic $f_{char}$ of a, to the contact body associated, sensor system oscillating in resonance, to thereafter press the contact body against the eye to form a new system oscillating in resonance, to read the contact force and the frequency characteristic for the new system, and to calculate the change in the frequency characteristic, whereby the pressure of the eye can be determined since the sought deformation area A is a function of the change $A(f_{char})$, calibrated for the actual sensor system. Calibration of the measurement instrument and measurement devices constitutes known moments and will therefore not be described in greater detail here.

The force with which the contact body is pressed against the eye can thus be adapted depending on the pressure of the eye so that a lower pressure is determined with a lower contact force against the eye and a higher pressure is determined with a higher contact force, whereby a high precision of measurement is obtained with minimum contact force over large intervals of pressure.

In an alternative embodiment, the frequency characteristic can be read continuously and the contact force F against the eye can be increased until a desired change in the frequency characteristic $\Delta f_{char}$ has been reached, whereby the contact force F can be read and the pressure calculated as a function of the contact force F at a specific change in the frequency characteristic $f_{char}$.

In a further embodiment, repeated readings can be made of the contact force F and the frequency characteristic while keeping the contact body pressed against the eye, whereby a series of measured values are obtained. A series of measured values increases the possibility of identifying and discarding measured values that fall outside the range of reliable measurements, for example, because the contact force was too low or because the force was so large that the deformation formed became larger than the area of contact.

During measurement and calculation of the frequency characteristic, components such as resonance frequency or phase can, for example, be used.

The enclosed FIGURE shows schematically a device according to one embodiment of the present invention. The device shows a sensor 1 arranged in position to measure the intraocular pressure in an eye 2. The sensor 1 is supported by an arrangement 3 for regulating the pressing of the sensor 1 against the eye. Arrangement 3 can control the force with which the sensor is pressed against the eye.

The sensor includes a contact body 4 having a contact area 5 that abuts the eye.

The contact body is supported in the sensor by, or it forms an integrated part of, an oscillating unit. In the embodiment shown, the oscillating unit 7 is a piezoelectric element. The piezoelectric element is appropriately suspended in a casing 10 that allows the piezo-electric element to swing as freely as possible. Attached to the piezoelectric element 7 is a smaller piezo-electric element 6, a so-called pick-up, firmly fixed, which is used to capture the oscillations in the piezo-electric element.

A means of driving is connected to the oscillating unit 7 to achieve its oscillating movement. In the present embodiment, a feedback circuit 8 is connected to the piezo-electric element 7 to feed back the oscillations registered by the pick-up 6 and to achieve a resonance oscillation in the system.

In the embodiment shown schematically in the FIGURE, the piezo-electric element 7 is connected to earth and to a band-pass filter BP. The pick-up 6 is glued firmly to the piezo-electric element 7 and connected to an amplifier Am, which in turn is connected to the band-pass filter BP for feed-back. Am and BP are tuned for optimal oscillation conditions, i.e. resonance frequency.

In addition, a means 9 for reading the frequency characteristic is connected to the system. This can be an ordinary frequency counter or another instrument suitable for signal processing.

Furthermore, it is advantageous if a calculator unit 11 is connected to the frequency counter for calculating the frequency difference.

In this embodiment, the contact surface is flat. The surface can, for example, be provided with a structure or pattern to displace the tear fluid. The contact surface can also be made concave with a radius of curvature that exceeds that of the surface of the eye against which it is intended to be pressed.

In a further embodiment, the contact surface can also be made convex. This is preferable when, for example, measuring the pressure of an eye that has a flat cornea. Flat corneas can, for example, be the result for someone who has undergone correction of their sight by smoothing the cornea by treatment with a laser, for example.

The contact body should be made of an electrically insulating material that prevents galvanic connections between the piezoelectric element and the eye. The contact body can advantageously be made of a polymer material. In addition, the contact body should have acoustic properties that allow frequencies to be transmitted to the eye. The piezo-electric element should be encased to avoid galvanic connections between the piezo-electric element and body of the patient or the treating person.

When the system is brought to oscillate in resonance and the frequency characteristic of the system has been read, the system is ready for measurement. Contact surface 5 is brought oscillating against an eye whose pressure is to be determined. The contact force and the frequency characteristic for the system then oscillating in resonance are then read. One or more readings can be taken for each occasion of measurement.

With the help of the previously made calibrations of the sensor system, the contact area can be interpreted from changes in frequency characteristic A($f_{char}$) and the pressure of the eye can be established.

To obtain reliable values, the area of the contact surface (5) must exceed that area that is formed when pressing against the eye.

The advantage of the method described here is obvious as it does not require a predetermined area of deformation and thus no lower limit of contact force for determining the pressure. Furthermore, the use of fluorescent chemicals in the eye is avoided.

As the device can be used for continuous measuring and gathering of information, it is also possible to study the pulsation in the intraocular pressure during a period of measurement. This pulsation can be affected by different underlying illnesses.

What is claimed is:

1. A method for measuring the intraocular pressure in an eye, the method comprising the steps of:

pressing a contact body with a known geometry against the eye with a force (F);

determining the area (A) of deformation of the eye;

calculating the pressure (P) from the correlation P=F/A;

reading the frequency characteristic ($\Delta f_{char}$) of the contact body associated with a sensor system oscillating in resonance;

pressing with a gradually increasing force (F) the contact body against the eye to cause change in the system oscillating in resonance;

continuously reading the contact force (F) and the frequency characteristic ($\Delta f_{char}$) for the system oscillating in resonance during deformation of the eye such that a series of measured values are obtained; and determining the relationship between the change in frequency characteristic ($\Delta f_{char}$) and force (F) to thereby determine the pressure (P) of the eye since the deformation area (A) sought is a function of the change in frequency characteristic ($\Delta f_{char}$).

2. The method according to claim 1, wherein the force which the contact body is pressed against the eye is chosen depending on the pressure of the eye such that a lower pressure is determined with a lower contact force against the eye and a higher pressure is determined with a higher contact force, whereby a high degree of measurement accuracy is obtained with a minimal contact force over a large pressure interval.

3. The method according to claim 1 wherein the frequency characteristic ($\Delta f_{char}$) is read continuously and the contact force (F) is increased until a desired change in the frequency characteristic ($\Delta f_{char}$) has been reached, the pressure (P) being determined as a function of the contact force (F) at a specified change of the frequency characteristic ($\Delta f_{char}$).

4. The method according to claim 1 wherein the frequency characteristic ($\Delta f_{char}$) is described by resonance frequency or a change in phase.

5. A device for measuring the intraocular pressure (P) in an eye, the device comprising:

a resonance oscillation system including a contact body (4) configured for pressing against an eye:

a reading device (9) connected to the resonance oscillation system and arranged to continuously read a frequency characteristic ($\Delta f_{char}$) of the system;

a measuring device (3) connected to the resonance oscillation system, and configured to continuously measure force with which the contact body is pressed against the eye;

a calculation device (11) connected to the reading device (9) and arranged to calculate the change in frequency characteristic ($\Delta f_{char}$); and a feedback device (8) connected to the reading device (9) and the resonance oscillation system, and arranged to read a force (F) with which the contact body is pressed against an eye;

wherein the device determines the frequency characteristic ($\Delta f_{char}$) and the force (F) to determine the pressure (P) of an eye.

6. The device according to claim 5, wherein the resonance oscillation system includes a piezo-electric element.

7. The device according to claim 5 or 6 wherein the contact body (4) has a flat contact surface (5) having a structure or a pattern.

8. The device according to claim 5 or 6 wherein the contact surface (5) is concave having a radius that exceeds the radius of the curvature of the surface of an eye against which it is intended to be pressed.

* * * * *